United States Patent
Beccaro et al.

(10) Patent No.: US 9,937,076 B2
(45) Date of Patent: Apr. 10, 2018

(54) VITRECTOMY APPARATUS

(71) Applicant: BBS S.R.L., Ponte San Nicolo (Padua) (IT)

(72) Inventors: Mauro Beccaro, Cadoneghe (IT); Enrico Bettini, Fiesso D'Artico (IT); Paolo Signori, Verona (IT); Mario Romano, Capri (IT)

(73) Assignee: AL.CHI.MI.A. S.R.L., Ponte San Nicolò (IT)

( * ) Notice: Subject to any disclaimer, the term of this patent is extended or adjusted under 35 U.S.C. 154(b) by 637 days.

(21) Appl. No.: 14/400,192

(22) PCT Filed: Jun. 6, 2013

(86) PCT No.: PCT/IB2013/054662
§ 371 (c)(1),
(2) Date: Nov. 10, 2014

(87) PCT Pub. No.: WO2013/183024
PCT Pub. Date: Dec. 12, 2013

(65) Prior Publication Data
US 2015/0126945 A1 May 7, 2015

(30) Foreign Application Priority Data

Jun. 8, 2012 (IT) .............................. VR2012A0122

(51) Int. Cl.
*A61F 9/007* (2006.01)
*A61B 17/00* (2006.01)
*A61B 18/00* (2006.01)

(52) U.S. Cl.
CPC .......... *A61F 9/007* (2013.01); *A61F 9/00736* (2013.01); *A61B 2017/00084* (2013.01);
(Continued)

(58) Field of Classification Search
CPC ................. A61F 9/00736; A61F 9/007; A61B 2017/00084; A61B 2018/00041;
(Continued)

(56) References Cited

U.S. PATENT DOCUMENTS

| 4,100,673 A | 7/1978 | Leavines |
| 4,523,086 A | 6/1985 | Eilentropp |

(Continued)

FOREIGN PATENT DOCUMENTS

| DE | 3346191 A1 | 7/1985 |
| DE | 102008062682 A1 | 3/2010 |

*Primary Examiner* — Adam Marcetich
(74) *Attorney, Agent, or Firm* — Pearne & Gordon LLP

(57) ABSTRACT

A vitrectomy apparatus comprises a containment body (3), at least one supply device (4), (5) which can be fixed to an eyeball (6) and/or moved by an operator, feeding means (7) for the controlled feeding of at least one operating fluid, at least partly mounted in the containment body (3) and in turn comprising at least one main pipe (8) which is or can be connected to the supply device (4), (5), and at least one control unit (21) operatively connected at least to the feeding means (7) for controlling their operation. The vitrectomy apparatus (1) also comprises means for varying the temperature (11) of the operating fluid, being coupled with the feeding means (7) and/or with the supply device (4), (5), for varying the temperature of the operating fluid, the control unit (21) also being connected to the means for varying the temperature (11) in order to control their operation. In particular, the means for varying the temperature (11) can act as heating means (12), and comprise one or more Peltier cells (15).

32 Claims, 8 Drawing Sheets

(52) U.S. Cl.
CPC ............... *A61B 2018/00035* (2013.01); *A61B 2018/00041* (2013.01); *A61B 2018/00791* (2013.01)

(58) Field of Classification Search
CPC ........... A61B 2018/00791; A61B 2018/00035; A61B 2018/00577
See application file for complete search history.

(56) References Cited

U.S. PATENT DOCUMENTS

| | | | |
|---|---|---|---|
| 4,725,713 A | 2/1988 | Lehrke | |
| 4,816,649 A | 3/1989 | Eilentropp | |
| 5,245,161 A | 9/1993 | Okamoto | |
| 5,542,928 A * | 8/1996 | Evans | A61B 18/082 604/113 |
| 5,616,120 A * | 4/1997 | Andrew | A61F 9/00736 604/28 |
| 5,910,266 A | 6/1999 | Jones | |
| 5,964,752 A * | 10/1999 | Stone | A61B 18/04 606/27 |
| 6,024,095 A * | 2/2000 | Stanley | A61B 18/04 128/898 |
| 6,602,227 B1 * | 8/2003 | Cimino | A61B 17/32006 604/113 |
| 2001/0051783 A1 * | 12/2001 | Edwards | A61B 18/1477 604/22 |
| 2006/0136022 A1 * | 6/2006 | Wong, Jr. | A61B 3/165 607/104 |
| 2008/0154197 A1 * | 6/2008 | Derrico | A61M 1/28 604/113 |
| 2009/0306640 A1 * | 12/2009 | Glaze | A61B 17/12045 606/27 |
| 2010/0126986 A1 | 5/2010 | Gunzing et al. | |
| 2010/0152724 A1 * | 6/2010 | Marion | A61B 5/01 606/33 |
| 2010/0168736 A1 * | 7/2010 | Wang | A61B 18/1492 606/41 |
| 2011/0077628 A1 * | 3/2011 | Hoey | A61B 18/04 606/27 |
| 2011/0144632 A1 | 6/2011 | Bourne et al. | |
| 2011/0144641 A1 | 6/2011 | Dimalanta et al. | |
| 2013/0079856 A1 * | 3/2013 | Dabrowiak | A61F 7/12 607/105 |

\* cited by examiner

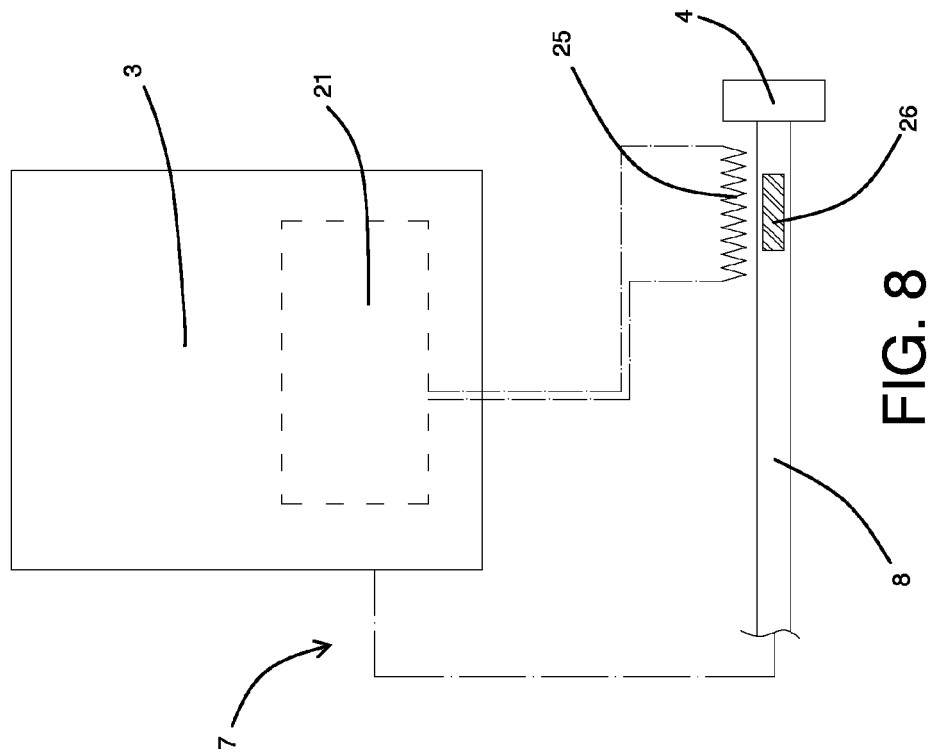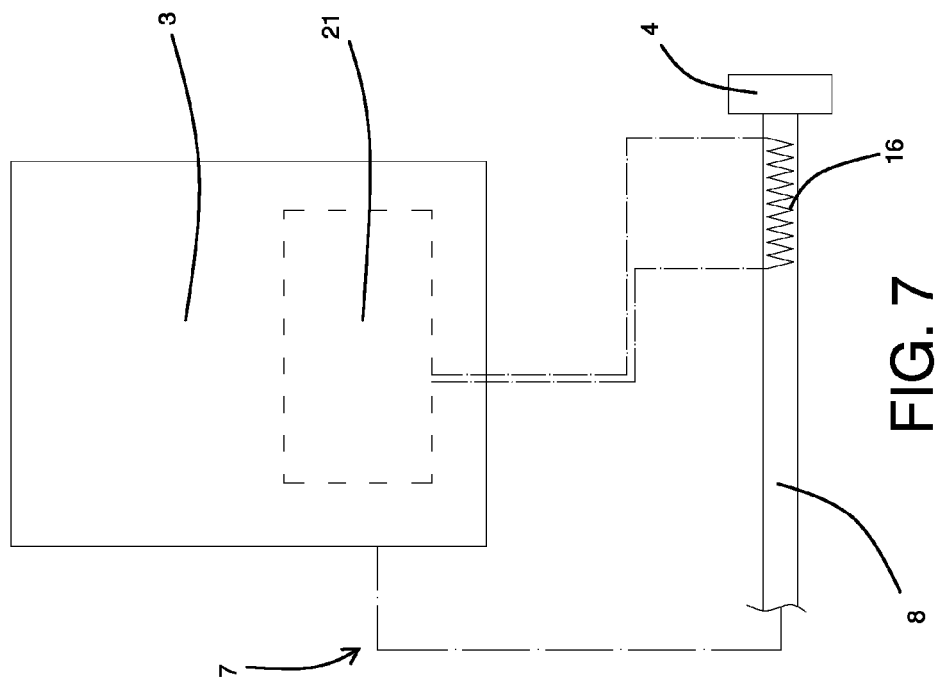

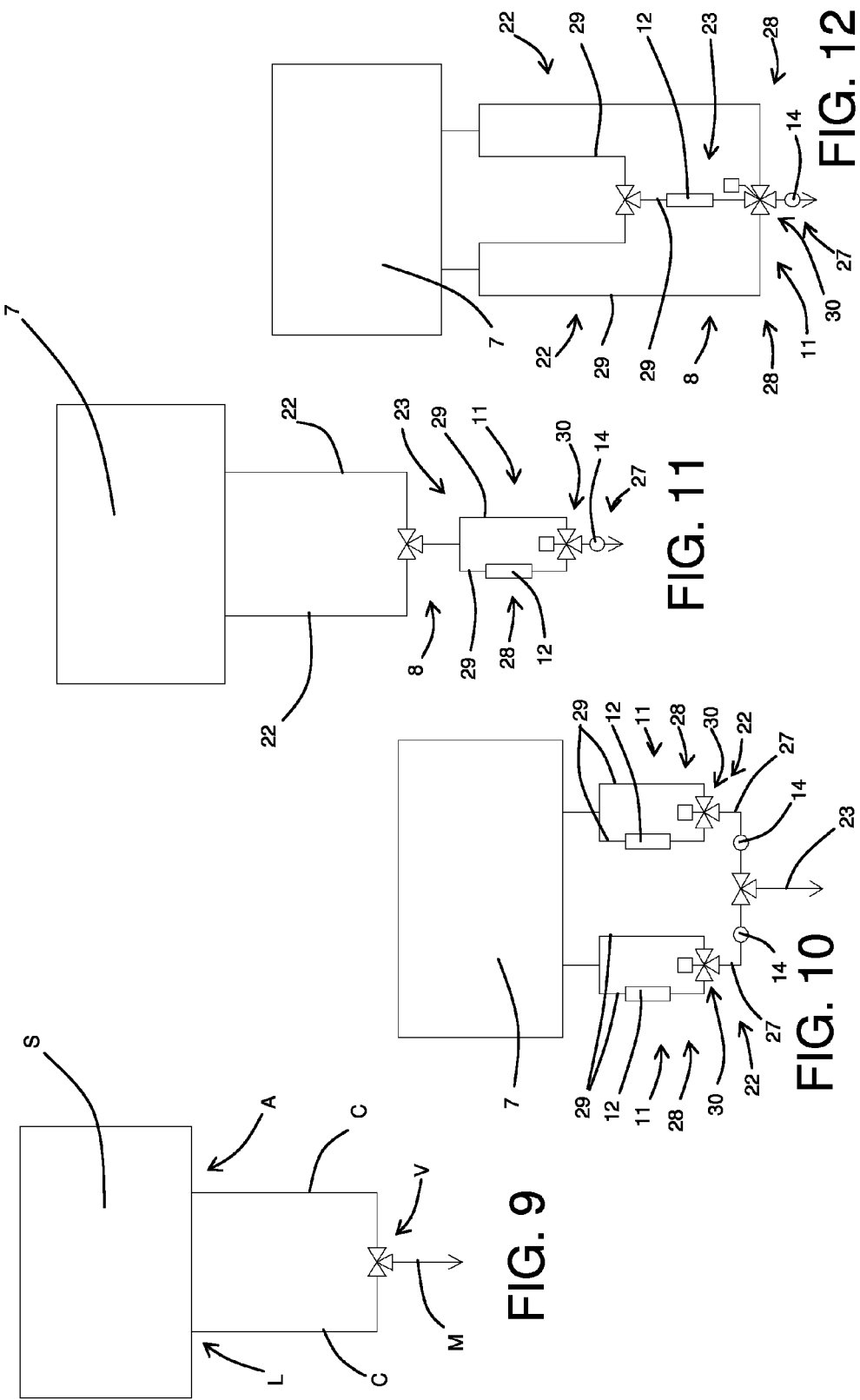

VITRECTOMY APPARATUS

TECHNICAL FIELD

This invention relates to a vitrectomy apparatus, that is to say, the apparatus usually used for vitreoretinal surgery.

In particular, this invention was devised relative to the typical function of vitrectomy apparatuses which allows the supply of an operating fluid inside the back chamber of an eyeball.

BACKGROUND ART

At present, vitrectomy apparatuses present on the market are complex, and complete in the sense that they are able to provide the surgeon with all of the functions that he may need during surgery.

Therefore, vitrectomy apparatuses are equipped with:
- an irrigation system through which they allow the supply of a liquid into the back chamber of the eye;
- a system for the continuous infusion of gas (sterile air) into the back chamber;
- a suction circuit which can also be connected to the eye, for sucking out both liquids and gases;
- and auxiliary pneumatic circuit for both controlling the operation of a second system for discontinuous infusion (pressurised air is used as a propellant for the fluid for infusion, such as a silicone oil) and for activating a first handpiece, that is to say, a device which the surgeon holds in his hand and uses for breaking up the vitreous humour. The handpiece usually comprises either microscissors or a blade or guillotine cutting edge, and may be either pneumatically activated (by means of the auxiliary pneumatic circuit) or electrically activated;
- a lighting circuit which powers a light source (usually an optical fibre) mounted on a second handpiece which the surgeon holds in his hand and inserts in the back chamber to make the operating area visible;
- a device for generating laser beams to be used for inducing a chiorientinal pexy;
- a control unit for controlling all of the various functions (computer);
- an interface for interaction with the control unit, normally consisting of a display and a keyboard and/or of a touch screen display;
- a control pedal for most of the functions; and
- a mobile instrument holder tray.

It should be noticed that both the supply of fluids into the back chamber and their suction out can be performed, depending on requirements, either by means of suitable pipes fixed to the eyeball at sclerotomies, or by means of handpieces operated by the surgeon.

However, during vitreoretinal surgery, usually three holes are made in the eyeball, a first hole where a supply device is fixed for supplying an operating fluid (liquid or gas) into the back chamber; a second hole through which the surgeon inserts a lighting handpiece/probe; and a third hole through which the surgeon on each occasion inserts the handpiece/tool used for the actual operation, that is to say, the handpiece/tool for breaking up and sucking out the vitreous humour, the one for injecting further fluid, the one used for the chiorientinal pexy, etc. In terms of its structure, the vitrectomy apparatus usually has a main body extending mainly vertically, mounted on wheels so that it can easily be moved, and in which the various systems, circuits and the devices listed above are installed. On the front side of the main body there are many infeed/outfeed ports/connections, for the connection of various accessories intended for the various applications.

For example, each vitrectomy apparatus may comprise a plurality of irrigation outfeeds for liquids which are the same or different, a plurality of infusion outfeeds for sterile air or other gases, one or more infusion outfeeds, one or more suction inlets for liquids and/or gases, one or more infeeds for liquids or gases for infusion, one or more lighting outfeeds, one or more connections for pneumatically supplying handpieces or discontinuous infusion devices, one or more outfeeds for producing the laser beam, etc.

Each connection allows the connecting up of various probes/tools/handpieces with which the surgeon can carry out the operation. Each probe/tool/handpiece is usually connected to the relative connection on the main body of the apparatus by a flexible connecting element, guaranteeing maximum freedom of movement.

The control unit is programmed and programmable for carrying out various functions (each unit may also allow the saving of hundreds of different programs) and can both manage the various functions in a fully automatic way depending on commands received via the interface, or manage one or more functions based on commands transmitted by the surgeon using the pedal during the operation.

For example, continuous irrigation and suction may be jointly controlled automatically so as to keep the intraocular pressure substantially stable (or rather, within a predetermined range) during an entire phase of the operation.

In contrast, the discontinuous infusion circuit is usually controlled directly by the surgeon using the pedal control.

Moreover, in the event of a suction error by the surgeon (for example of the retina), the vitrectomy apparatus allows the surgeon to activate, with the pedal, a function which produces a fluid reflux through the handpiece which is normally only used for suction.

Although vitrectomy apparatuses are relatively complex, as already indicated, this invention relates exclusively to their capacity for directly supplying fluids into the back chamber (therefore, usually the irrigation and infusion of sterile liquid or air, whilst it excludes the infusion of substances by means of the pneumatic push circuit). A diagram of a system for feeding air or liquid currently widely used in vitrectomy apparatuses is illustrated in FIG. 9, which shows how the feeding system S has two outfeeds, one outfeed A for the air and one outfeed L for the liquid. Connected to the two outfeeds there are two pipes C which connect them to two infeed ports of a three-way switching valve V. The main pipe M to the supply device to be used in the eye is connected to the valve outfeed. In this case, switching between supplying air or liquid into the eye is performed by the surgeon by simply switching the valve V. This invention was devised in particular with reference to several problems which may arise during surgery involving the vitreous humour performed using vitrectomy apparatuses, although said problems are not actually caused by the vitrectomy apparatuses.

First, it has been seen that, in particular after vitrectomy operations, there may be damage to the endo-ocular circulatory system, including inhibited platelets, inhibited clotting factors, loss of electrolytes, etc.

Second, it has been found that in most vitreoretinal surgeries it is quite difficult to completely remove from the eye the substances used as endo-ocular tamponades, such as liquid perfluorocarbons, and that the related residues remaining in the eye subsequently cause inflammatory and proliferative phenomena affecting the retina and intraocular tissues. The presence of such residues may also modify the physical and rheological properties of the tamponades used post-operatively, causing potential iatrogenic damage to the intraocular structures.

DISCLOSURE OF THE INVENTION

In this context the technical purpose which forms the basis of this invention is to provide a vitrectomy apparatus which overcomes the above-mentioned disadvantages.

In particular, the technical purpose of this invention is to provide a vitrectomy apparatus which allows easier removal of the substances used as endo-ocular tamponades, such as perfluorocarbons, compared with the prior art apparatuses.

The technical purpose of this invention is also to provide a vitrectomy apparatus which allows a reduction in the risk of causing damage both to the endo-ocular circulatory system and to the ocular structures.

The technical purpose specified and the aims indicated are substantially achieved by a vitrectomy apparatus made as described in the appended claims.

BRIEF DESCRIPTION OF THE DRAWINGS

Further features and the advantages of this invention are more apparent in the detailed description, with reference to the accompanying drawings which illustrate several preferred, non-limiting embodiments of a vitrectomy apparatus, in which:

FIG. 7 is a schematic view of a detail of the vitrectomy apparatus of FIG. 1 made in accordance with a sixth embodiment;

FIG. 8 is a schematic view of a detail of the vitrectomy apparatus of FIG. 1 made in accordance with a seventh embodiment;

FIG. 9 is a schematic view of a type of vitrectomy apparatus made in accordance with the prior art;

FIG. 10 is a schematic view of a first version modified in accordance with this invention of the vitrectomy apparatus of FIG. 9;

FIG. 11 is a schematic view of a second version modified in accordance with this invention of the vitrectomy apparatus of FIG. 9; and FIG. 12 is a schematic view of a third version modified in accordance with this invention of the vitrectomy apparatus of FIG. 9.

DETAILED DESCRIPTION OF PREFERRED EMBODIMENTS OF THE INVENTION

Figure 1:
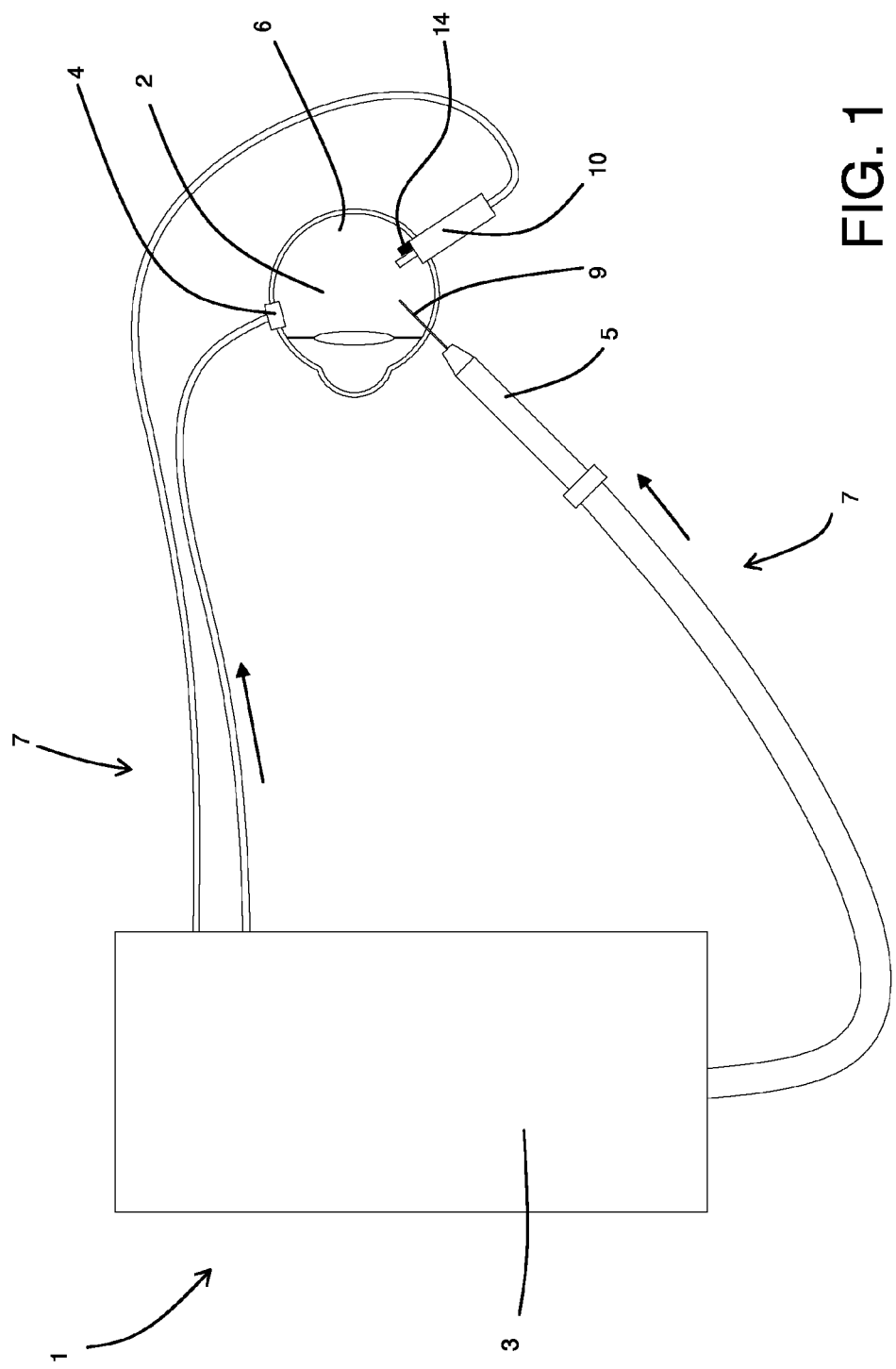
FIG. 1 schematically illustrates a vitrectomy apparatus made in accordance with this invention, limited to several of its parts of interest for this invention (and with reference to their use in an eye)

With reference to the accompanying drawings the numeral 1 denotes in its entirety a vitrectomy apparatus made in accordance with this invention. However, since, as already indicated, this invention relates exclusively to some of the functions of the vitrectomy apparatus 1, those linked to using the vitrectomy apparatus 1 for supplying fluids into the back chamber 2 of the eye, in the accompanying drawings the vitrectomy apparatus 1 is very schematically illustrated and only some details linked to these functions of it are shown, again schematically. All of the other functions of the vitrectomy apparatus 1 to which this invention does not directly relate, although not illustrated or described below, may in any case vary according to requirements, and in particular may be as in the prior art.

Therefore, in general, the vitrectomy apparatus 1 according to this invention comprises a containment body 3, at least one supply device 4, 5 which can be handled by an operator or fixed to an eyeball 6, and feeding means 7 for the controlled feeding of at least one operating fluid to the supply device 4, 5.

In particular, in the known way, the feeding means 7 are at least partly mounted in the containment body 3 and comprise at least one main pipe which is or can be connected to the supply device 4, 5. In any case, the feeding means 7 are of the known type and therefore are not described in any further detail herein. Depending on requirements, the vitrectomy apparatus 1 may comprise a plurality of supply devices 4, 5, each fed or feedable through a respective main pipe 8, and which can be connected either in parallel or alternatively to the feeding means 7. Each main pipe 8 is also at least partly flexible for facilitating the movement of the respective supply device 4, 5.

The embodiment illustrated in FIG. 1, in particular, shows the case in which the apparatus simultaneously comprises two supply devices 4, 5, a first supply device of the fixed type (hereinafter the fixed supply device 4) which in use is fixed at a sclerotomy made in the eyeball 6, and a second supply device of the free type (hereinafter the free supply device 5) which can be gripped by the operator and is equipped with a needle-shaped injection nozzle 9 (therefore, this second free supply device 5 is a handpiece).

However, in general, the vitrectomy apparatus 1 may comprise both fixed supply devices 4 and free supply devices 5, and each may be intended both for irrigating the eye with a liquid (such as a balanced salt solution—BSS) or for infusing gas (such as sterile air) into it. Therefore, it may also be the case that two or more main pipes 8 may be connected or connectable to a single supply device 4, 5, for example one for a liquid operating fluid and one for a gaseous operating fluid. In this case, as explained in more detail below, even in accordance with this invention the structure may be similar to that of conventional vitrectomy apparatuses (illustrated in FIG. 9). In particular, the feeding means 7, which, as already indicated, feed at least a first operating fluid and a second operating fluid which are separate, respectively comprise a first main pipe 8a for the first fluid and a second main pipe 8b for the second fluid. However, the first main pipe 8a and the second main pipe 8b comprise a separate initial stretch 22 and a shared final stretch 23, there being interposed between the initial stretches and the final stretch a three-way switching valve 24 comprising two infeed sections each connected to one of the initial stretches 23, and one outfeed section connected to the final stretch 23. Switching the switching valve 24 between the two infeed sections it is therefore possible to selectively feed to the supply device 4, 5 either the first fluid or the second fluid.

Moreover, similarly to the prior art vitrectomy apparatuses, even the one according to this invention comprises at least a control unit 21 (only illustrated in the embodiments of FIGS. 2 and 3) operatively connected at least to the feeding means 7 for controlling their operation (in particular the way in which the fluid is supplied), and, preferably, the user can interact with the control unit 21 either by means of a known type of control interface (which may therefore include a display and keyboard which are not illustrated herein) or by means of a control pedal, also of the known type (and also not illustrated).

The control unit 21 may also be programmed to perform any of the functions currently known relative to a vitrectomy apparatus 1.

With reference to the characteristic aspect of this invention, the vitrectomy apparatus 1 also comprises means for varying the temperature 11 of the operating fluid, for varying the temperature of the operating fluid which is supplied by the vitrectomy apparatus 1 into the eye.

As described in more detail below, the means for varying the temperature 11 are preferably coupled with the feeding means 7, but if necessary may also or only be coupled with the supply device 4, 5. In particular, the means for varying the temperature 11 are preferably at least partly mounted around at least part of the main pipe 8, or inside it, for varying the temperature of the operating fluid while it flows through the main pipe 8. However, advantageously, since the temperatures involved must never cause problems to the structures of the eye, in the context of this invention the temperature variations referred to are always at most several dozen degrees Centigrade. In particular, the variation of the temperature of the operating fluid is controlled in such a way as to obtain a temperature range within the eye which is at most around twenty degrees Centigrade, for example between a minimum temperature of 15° C. and a maximum temperature of 37° C. That can be achieved either with a corresponding variation to the temperature of the operating fluid, so as to be able to reach a substantially uniform temperature after a relatively long time, or by causing a greater temperature variation in the operating fluid, for obtaining the desired temperature after mixing a predetermined quantity of operating fluid with the fluid present in the back chamber of the eye, after a time which is usually shorter than in the former case. For example, to raise the temperature of the back chamber from 22° C. to 28° C., it is possible either to injection operating fluid at 28° C. (with the prospect of achieving the desired result after a relatively long time, substantially needed to substitute all of the fluid at 22° C. with the operating fluid at 28° C.), or by injecting a smaller quantity of operating fluid for example at 37° C. (to achieve the desired final temperature by mixing the "hot" operating fluid with the "cold" fluid already present).

According to a first simplified, preferred embodiment, the means for varying the temperature 11 comprise exclusively heating means 12 for allowing an increase in the temperature of the operating fluid supplied.

In contrast, according to a second, more complete embodiment, the means for varying the temperature 11 also comprise cooling means 13 for reducing the temperature of the operating fluid supplied and therefore allowing complete regulation of its temperature.

The control unit 21 is usually connected to the means for varying the temperature 11, for controlling their operation based both on saved programming, or any commands issued by the user (for example via the interface), advantageously based on the criteria indicated above.

In the preferred embodiment, to guarantee improved control of the means for varying the temperature 11, the control unit 21 is programmed to control the means for varying the temperature 11 also according to the signal received from a temperature detector 14 (only illustrated in FIGS. 1 and 2) mounted in such a way that, in use, it can detect either the temperature of the operating fluid supplied or the internal temperature of the eyeball 6 at the back chamber 2. In fact, the temperature detector 14 is connected to the control unit 21 for sending it a signal indicating the temperature detected, that is to say, preferably either a signal representative of the temperature value detected, or a signal indicating if the temperature detected has gone beyond (in a positive or negative sense) a predetermined threshold value.

Figure 2:
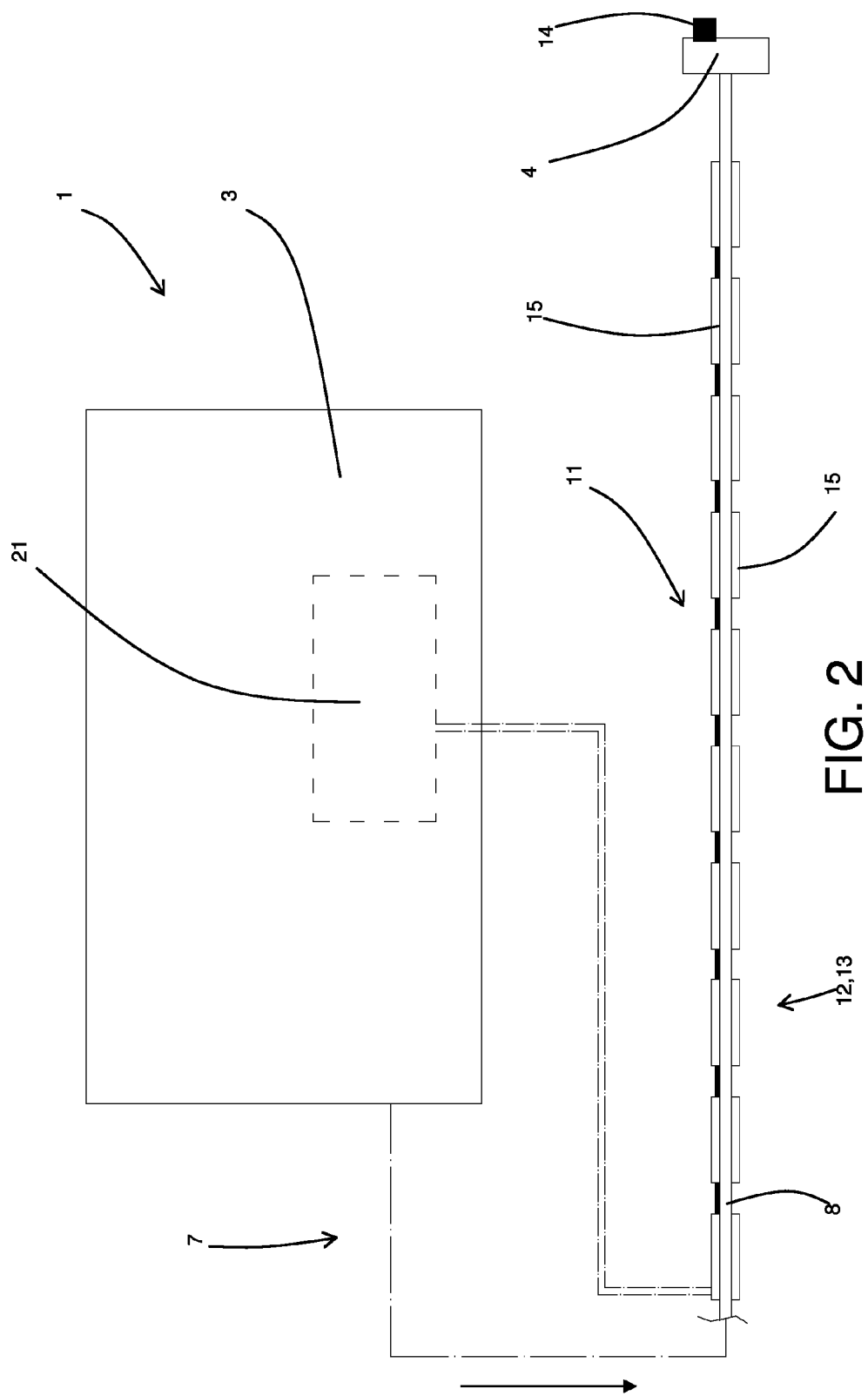
FIG. 2 is a schematic view of a detail of the vitrectomy apparatus of FIG. 1 made in accordance with a first embodiment of this invention.

As already indicated, the temperature detector 14 may be associated with the supply device 4, 5 for measuring the temperature of the fluid supplied (solution illustrated in FIG. 2). However, in a first preferred embodiment it is, in contrast, mounted in such a way that it can detect the internal temperature of the eye, since this is the most important temperature for achieving the desired results. Therefore, preferably, the detector 14 is mounted on a different supporting element 10 which can be inserted in the eyeball 6, for example, as shown in FIG. 1, the handpiece used by the surgeon for lighting the back chamber 2 (which is connected to a related outfeed of the containment body 3, and inside which an optical fibre is mounted for providing the lighting). As is explained in more detail below, in a different preferred embodiment, in contrast the temperature detector 14 is mounted in the main pipe 8 for detecting the temperature of the operating fluid downstream of the means for varying the temperature 11.

Advantageously, the control interface is set up to allow the user to set a reference temperature, and it is connected to the control unit 21 for communicating said reference temperature to it. In this way, the control unit 21 can be programmed to control the means for varying the temperature 11 also depending on the reference temperature set using the control interface. However, in other embodiments the reference temperature may already be saved in the control unit 21.

Depending on requirements and the embodiments of this invention, the means for varying the temperature 11 may adopt various configurations, some of which are schematically illustrated in FIGS. 2 to 8.

In a first embodiment of this invention, the means for varying the temperature 11 comprise one or more Peltier cells 15 which are associated with the pipe and/or with the supply device 4, 5. In particular, FIG. 2 shows the case in which there is a plurality of Peltier cells 15 connected to the control unit 21 and controlled by it. The cells are mounted one after another along the pipe. It should be noticed that when two or more separate cells are present they are preferably controlled independently so as to guarantee greater versatility of the means for varying the temperature. In fact, at any moment it is possible to activate from a single cell to all of the cells present. As is known, Peltier cells 15 are small solid state heat pumps able to transfer heat between two opposite surfaces depending on the polarity used to supply the semiconductors of which they consist. Moreover, they are particularly advantageous when the thermal gradient is low and energy efficiency is not particularly important, as is the case for this invention.

Figure 3:
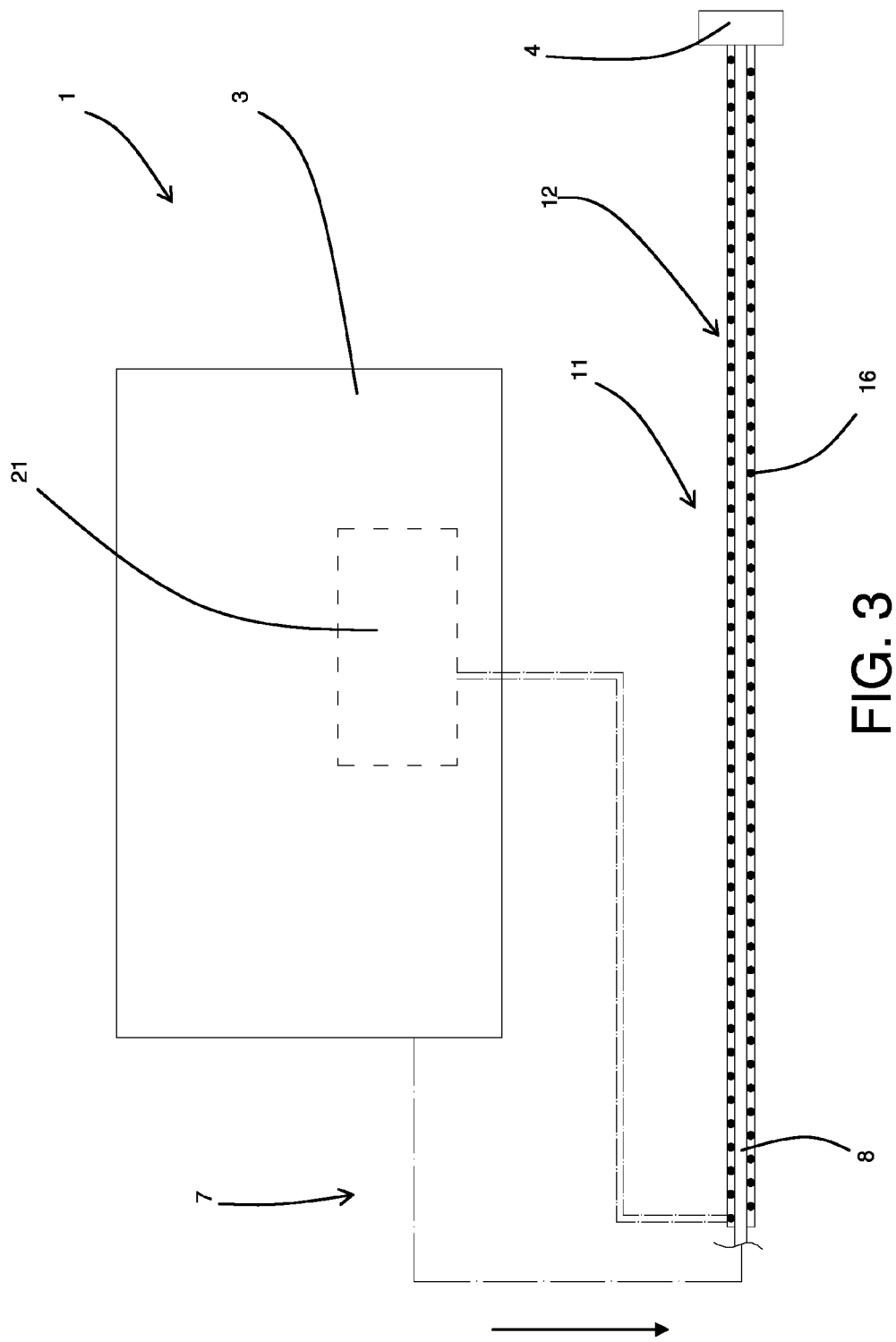
FIG. 3 is a schematic view of a detail of the vitrectomy apparatus of FIG. 1 made in accordance with a second embodiment of this invention.

In contrast, FIG. 3 shows the case in which the heating means 12 comprise one or more electric heating elements 16 mounted around the main pipe 8 (in the case illustrated in particular there is a single heating element).

In particular, in the known way, the heating elements 16 may be of the type described for example in patents U.S. Pat. No. 5,245,161, U.S. Pat. No. 4,816,649, U.S. Pat. No. 4,523,086, U.S. Pat. No. 4,725,713, US 2010126986, DE 3346191, DE 102008062682, U.S. Pat. No. 5,910,266 and U.S. Pat. No. 4,100,673. As shown in FIG. 7, alternatively the heating means 12 comprise one or more electric heating elements 16 mounted inside the main pipe 8.

Figure 4:
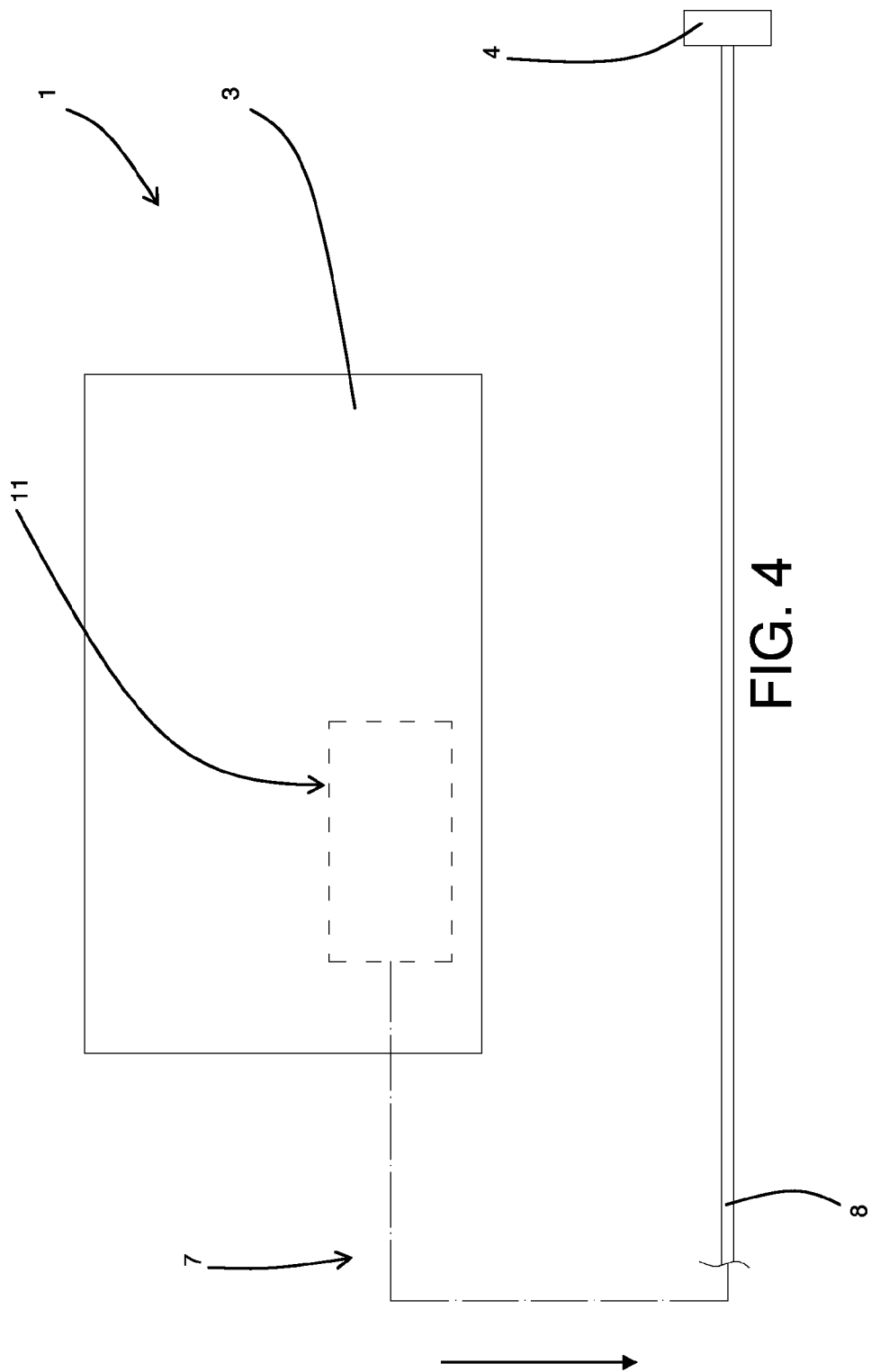
FIG. 4 is a schematic view of a detail of the vitrectomy apparatus of FIG. 1 made in accordance with a third embodiment of this invention.

The embodiment in FIG. 4 is a schematic illustration of the case in which the means for varying the temperature 11 are directly associated with the part of the feeding means 7 which feeds the operating fluid to the main pipe 8. In this way, depending whether the means for varying the temperature 11 are heating means 12, cooling means or both, the operating fluid is supplied already either heated or cooled.

In contrast, in a further embodiment the means for varying the temperature 11 comprise at least one secondary pipe 17 mounted on the outside of and coaxially with at least part of the main pipe 8. A feeding device 18 is connected to the secondary pipe 17 for feeding it with a secondary fluid having a controlled temperature, used for causing a variation in the temperature of the operating fluid after a heat exchange between the main pipe 8 and the secondary pipe 17.

The feeding device 18 is in turn controlled by the control unit 21 and may therefore vary the temperature of the secondary fluid based on the commands received from the control unit 21.

Figure 5:
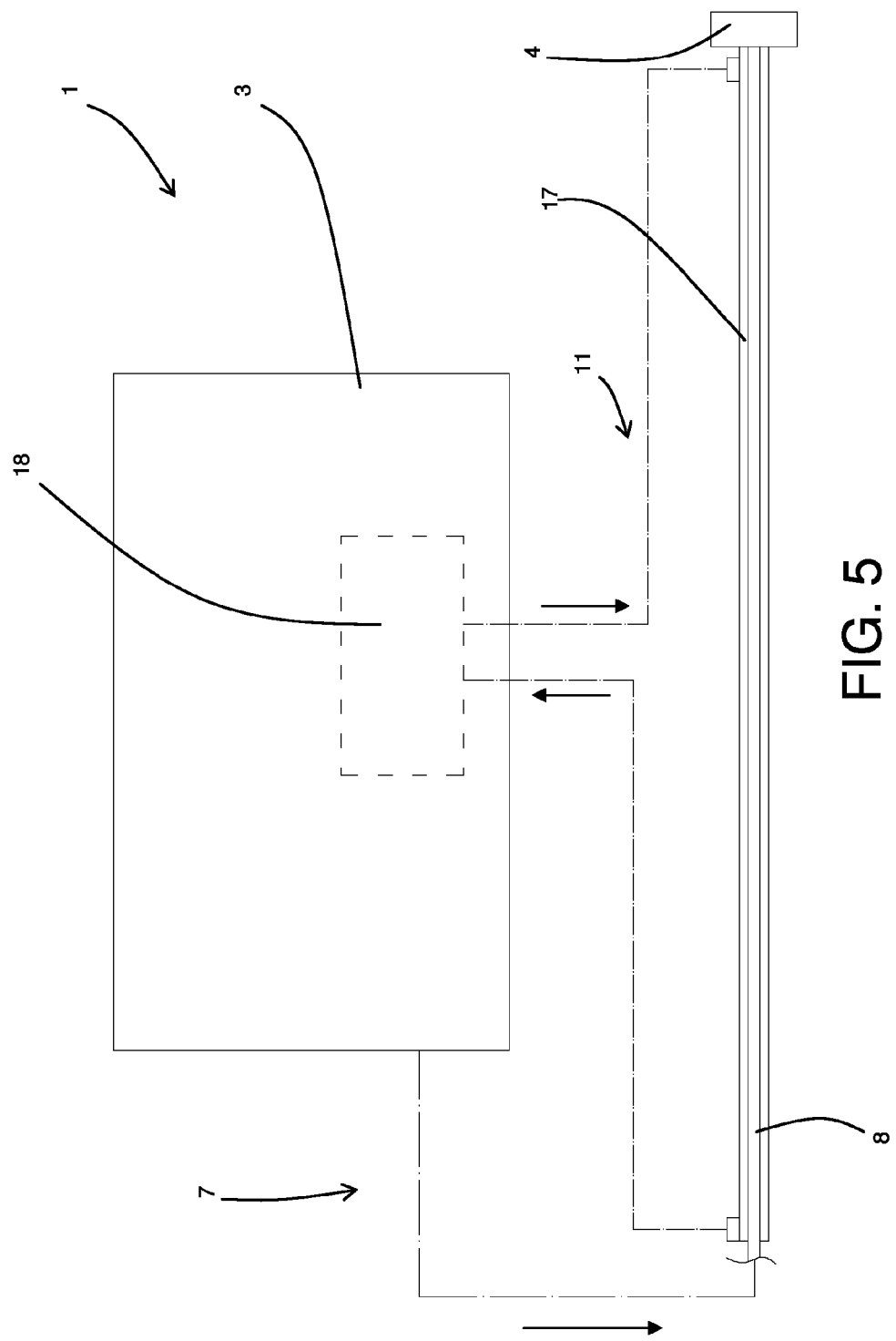
FIG. 5 is a schematic view of a detail of the vitrectomy apparatus of FIG. 1 made in accordance with a fourth embodiment of this invention.

The embodiment in FIG. 5 shows the case of a single feeding device 18 which may be able to exclusively heat (for example using electric heating elements 16) or cool (for example using a refrigerating circuit), or to perform both operations (using a system of Peltier cells 15 or using a conventional type of heat pump). The feeding device 18 delivery side is advantageously connected to the end of the main pipe 8 closest to the supply device 4, 5, whilst its return side is connected to the end of the secondary pipe 17 furthest from the supply device 4, 5.

Figure 6:
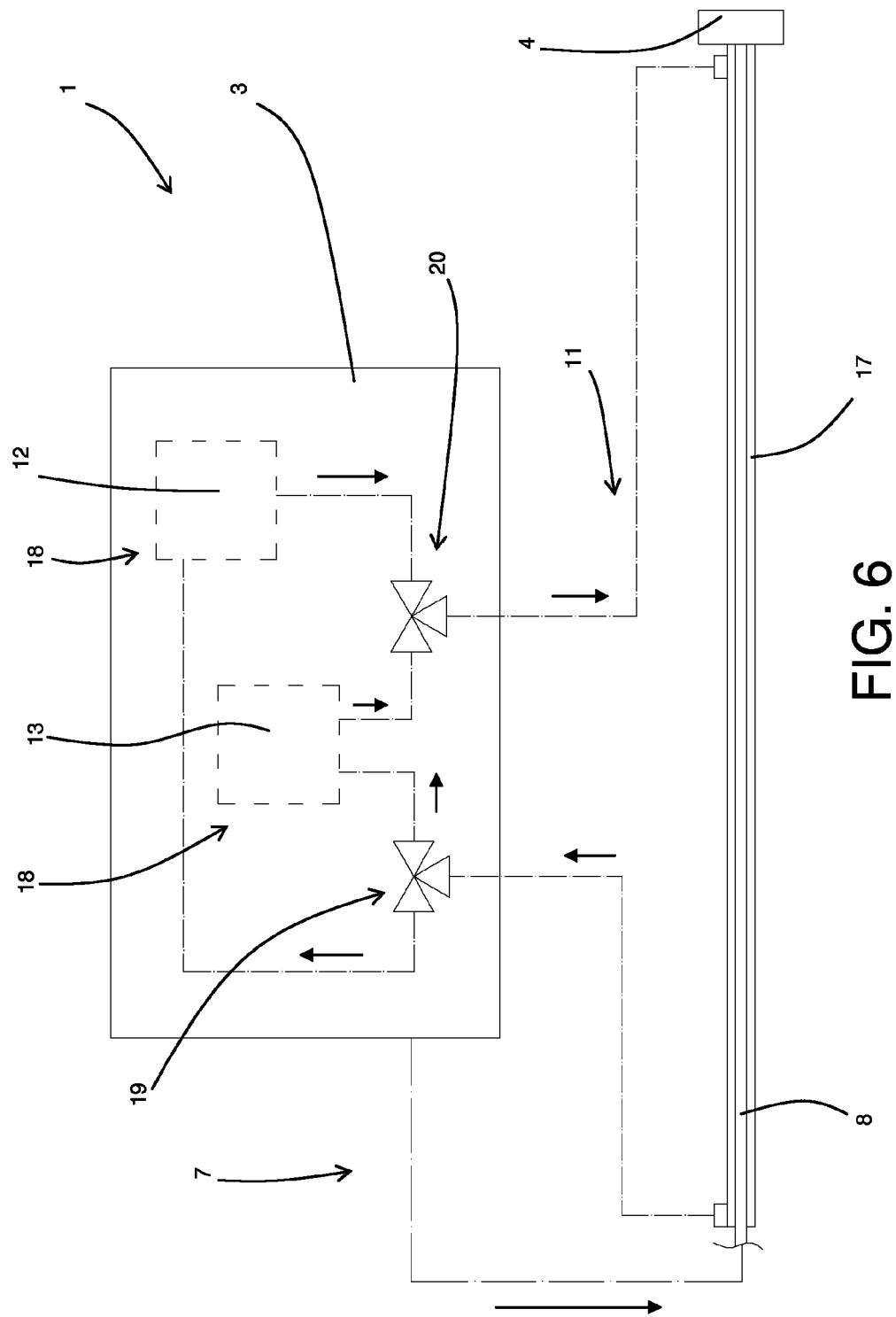
FIG. 6 is a schematic view of a detail of the vitrectomy apparatus of FIG. 1 made in accordance with a fifth embodiment.

In contrast, in the embodiment in FIG. 6 there are two feeding devices 18, one exclusively able to heat the secondary fluid, and the other exclusively able to cool it. The respective delivery sides are advantageously each connected to an infeed of a first three-way valve 19, whose outfeed is in turn connected to the end of the main pipe 8 closest to the supply device 4, 5. Similarly, the two return sides of the feeding devices 18 are advantageously each connected to an infeed of a second three-way valve 20, whose outfeed is in turn connected to the end of the secondary pipe 17 furthest from the supply device 4, 5. With that structure, by simply switching the two three-way valves 19, 20 is it possible, depending on requirements, to feed the secondary pipe 17 with heated or cooled fluid.

Finally, FIG. 8 shows an embodiment in which the heating means 12 comprise one or more inductors 25 mounted around the main pipe 8 and one or more conductive elements 26 inserted in the main pipe 8 and electromagnetically coupled with the one or more inductors 25 in such a way that the circulation of current in the inductors 25 causes the circulation of eddy currents in the conductive elements 26. The latter will be made of a material with an electric resistance value such that it allows the circulation of a current sufficient for heating them.

Although all of the embodiments of the Figures from 2 to 8 are illustrated with reference to a fixed supply device 4, similar solutions may also be adopted for free supply devices 5.

FIGS. 10 to 12 show several possible alternative embodiments of the circuits of the feeding means 7, which aim to guarantee that the temperature of the operating fluid remains more constant as time passes. Although the various alternative embodiments illustrated refer to embodiments of the type described above in which the feeding means 7 feed at least a first operating fluid and a second operating fluid which are separate, and respectively comprise a first main pipe 8a and a second main pipe 8b with a separate initial stretch 22 and a shared final stretch 23 and a switching valve 24 interposed between the initial and final stretches, what is described below shall be considered applicable, with the necessary devices, also to a single main pipe 8 for a single operating fluid.

In general, the idea which forms the basis of all of these embodiments is to create, in parallel with the branch of the main pipe 8 where the means for varying the temperature 11 act, a branch without means for varying the temperature, and to mix the operating fluid whose temperature has been varied, with the operating fluid whose temperature is unchanged, so as to achieve the desired final temperature. By modulating the mixing using a control based on detection of the temperature of the mixed operating fluid (carried out by the temperature detector 14 mounted in the main pipe 8), it is possible to precisely control the temperature of the operating fluid irrespective of the operating precision of the means for varying the temperature 11.

In more detail, each main pipe 8 comprises at least a downstream stretch 27 which is or can be connected to the supply device 4, 5, and an upstream stretch 28 comprising at least two parallel ducts 29 which are or can be fed with the same operating fluid. Interposed between the upstream stretch 28 and the downstream stretch 27 there is at least one mixing valve 30 comprising at least two infeeds each connected to one of the two parallel ducts 29, and one outfeed connected to the downstream stretch 27. The means for varying the temperature 11 are coupled with one of the two ducts 29, for varying the temperature of the operating fluid in that duct relative to that in the other duct.

In the embodiment in FIG. 10, the two ducts 29 of each main pipe 8 are made in the initial stretch 22 of each main pipe upstream of the switching valve 24.

In the embodiment in FIG. 11, the two ducts 29 of each main pipe 8 coincide and are made in the shared downstream stretch 27 of the two main pipes 8.

Finally, in the embodiment in FIG. 12, for each main pipe the two ducts 29 are made at least at part of the initial stretch 22 and part of the final stretch 23. Moreover, at said part of the final stretch 23 the two main pipes share one of the two ducts 29. The means for varying the temperature 11 are mounted at this shared duct 29. In the embodiment illustrated the mixing valve 30 is a four-way 29 valve and comprises three infeeds, each connected to one of the ducts 29, and one outfeed which is connected to the remaining shared final stretch 23. The mixing valve 30 is also structured to allow alternatively the mixing of the fluid arriving from the shared duct with that arriving from only one of the other two ducts 29. However, the same result could be achieved using two three-way 29 mixing valves.

In all of the embodiments requiring mixing, the temperature detector 14 is advantageously mounted in the main pipe downstream of the mixing valve 30, and the mixing valve 30 is connected to the control unit 21 which is programmed to control the mixing valve 30 depending on what is detected by the temperature detector 14.

This invention brings important advantages.

First, when the means for varying the temperature are heating means, it is possible to facilitate the removal of substances used as endo-ocular tamponades. In particular, by supplying a heated fluid into the eye it is possible to bring the temperature of the back chamber from the 22-24° C. normally present during an operation, to around 28-30° C. If the tamponade used is a perfluorocarbon the temperature increase tends to make it gather together in a single bubble which is easier for the surgeon to suck out. If instead the tamponade is a viscous substance, such as silicone oil, the temperature increase tends to increase its fluidity, again facilitating its removal by suction performed by the surgeon.

Second, again when the means for varying the temperature are heating means, supplying heated air inside the eye, for example by again bringing the temperature to around 28-30° C., it is possible to facilitate the elimination of any endo-ocular tamponade residues that were not previously sucked out, by evaporating them. In fact, it has been seen that the vapour pressure, for example for perfluorocarbons, significantly increases with an increase in the temperature of the back chamber even by just a few degrees Centigrade.

In contrast, when the means for varying the temperature are also cooling means, it is possible to use irrigation with a cooled fluid to offset the temperature increase caused by the laser during the retina reattachment stage, thereby preventing damage to the endo-ocular circulatory system due to localised overheating caused by the laser.

Finally, it should be noticed that this invention is relatively easy to produce and that even the cost linked to implementing the invention is not very high.

The invention described above may be modified and adapted in several ways without thereby departing from the scope of the inventive concept. Moreover, all details of the invention may be substituted with other technically equivalent elements and the materials used, as well as the shapes and dimensions of the various components, may vary according to requirements.

The invention claimed is:

1. A vitrectomy apparatus comprising:
   a containment body (3);
   at least one supply device (4), (5) configured to communicate fluidly with an eyeball (6)
   feeding means (7) for controlled feeding of at least one operating fluid, said means being at least partly mounted in the containment body (3) and in turn comprising at least one main pipe (8) which is or can be connected to the supply device (4), (5); and
   at least one control unit (21) operatively connected at least to the feeding means (7) for controlling their operation;
   wherein the vitrectomy apparatus also comprises means for varying the temperature (11) of said operating fluid, said means for varying the temperature being coupled with the feeding means (7) and/or with the supply device (4), (5), and being effective for varying the temperature of the operating fluid within the range 15° C.-37° C., the control unit (21) also being connected to the means for varying the temperature (11) in order to control operation of said means for varying the temperature (11).

2. The vitrectomy apparatus according to claim 1, wherein it also comprises at least one temperature detector (14) for in use detecting either the temperature of the operating fluid supplied or the internal temperature of the eyeball (6), the detector (14) being connected to the control unit (21) for sending said control unit a signal indicating the temperature detected, and the control unit (21) being programmed to control the means for varying the temperature (11) depending on the signal received from the detector (14).

3. The vitrectomy apparatus according to claim 2, wherein the detector (14) is fixed to the supply device (4), (5) or is mounted on a different supporting element (10) which is configured so that it can be inserted in said eyeball (6).

4. The vitrectomy apparatus according to claim 2, wherein it also comprises at least one control interface through which it is possible to set a reference temperature, connected to the control unit (21) for communicating said reference temperature to it, the control unit (21) being programmed to control the means for varying the temperature (11) also depending on the reference temperature set using the control interface.

5. The vitrectomy apparatus according to claim 1, wherein the means for varying the temperature (11) comprise heating means (12) for increasing the temperature of the operating fluid supplied.

6. The vitrectomy apparatus according to claim 5, wherein the means for varying the temperature (11) also comprise cooling means (13) for reducing the temperature of the operating fluid supplied.

7. The vitrectomy apparatus according to claim 5, wherein the means for varying the temperature (11) comprise one or more Peltier cells (5) which are associated with said pipe and/or with said supply device (4), (5).

8. The vitrectomy apparatus according to claim 5, wherein the heating means (12) comprise one or more electric heating elements (16) mounted around the main pipe (8).

9. The vitrectomy apparatus according to claim 5, wherein the heating means (12) comprise one or more electric heating elements (16) mounted inside the main pipe (8).

10. The vitrectomy apparatus according to claim 5, wherein the heating means (12) comprise one or more inductors (25) mounted around the main pipe (8) and one or more conductive elements (26) inserted in the main pipe (8) and electromagnetically coupled with the one or more inductors (25) in such a way that the circulation of current in the inductors (25) causes the circulation of eddy currents in the conductive elements (26).

11. The vitrectomy apparatus according to claim 5, wherein the means for varying the temperature (11) are at least partly mounted around at least part of said main pipe (8) for varying the temperature of the operating fluid while it flows through the main pipe (8).

12. The vitrectomy apparatus according to claim 5, wherein the feeding means (7) feed at least a first operating fluid and a second operating fluid which are separate, said means respectively comprising a first main pipe (8a) for the first fluid and a second main pipe (8b) for the second fluid, the first main pipe (8a) and the second main pipe (8b) comprising a separate initial stretch (22) and a shared final stretch (23), there being interposed between the initial stretches (23) and the final stretch (23) a three-way (29) switching valve (24) comprising two infeed sections each connected to one of the initial stretches (23), and one outfeed section connected to the final stretch (23).

13. The vitrectomy apparatus according to claim 5, wherein the main pipe (8) comprises at least a downstream stretch (27) which is or can be connected to the supply device (4), (5), and an upstream stretch (28) comprising at least two parallel ducts (29) which are or can be fed with the same operating fluid, there being interposed between the upstream stretch (28) and the downstream stretch (27) at least one mixing valve (30) comprising at least two infeeds each connected to one of the two parallel ducts (29), and one outfeed connected to the downstream stretch (27), and in that the means for varying the temperature (11) are coupled with one of the two ducts (29), for varying the temperature of the operating fluid in that duct relative to that in the other duct.

14. The vitrectomy apparatus according to claim 1, wherein the means for varying the temperature (11) comprise at least one secondary pipe (17) mounted on the outside of and coaxially with at least part of the main pipe (8), and which can be fed with a secondary fluid at a controlled temperature for causing a variation in the temperature of the operating fluid, and at least one device (18) for feeding the secondary fluid to the secondary pipe (17), the feeding device (18) being controlled by the control unit (21) and varying the temperature of the secondary fluid.

15. The vitrectomy apparatus according to claim 1, wherein the means for varying the temperature (11) are at least partly mounted around at least part of said main pipe (8) for varying the temperature of the operating fluid while it flows through the main pipe (8).

16. The vitrectomy apparatus according to claim 1, wherein the feeding means (7) feed at least a first operating fluid and a second operating fluid which are separate, said means respectively comprising a first main pipe (8a) for the first fluid and a second main pipe (8b) for the second fluid, the first main pipe (8a) and the second main pipe (8b) comprising a separate initial stretch (22) and a shared final stretch (23), there being interposed between the initial stretches (23) and the final stretch (23) a three-way (29) switching valve (24) comprising two infeed sections each connected to one of the initial stretches (23), and one outfeed section connected to the final stretch (23).

17. The vitrectomy apparatus according to claim 16, wherein the main pipe (8) comprises at least a downstream stretch (27) which is or can be connected to the supply device (4), (5), and an upstream stretch (28) comprising at least two parallel ducts (29) which are or can be fed with the same operating fluid, there being interposed between the upstream stretch (28) and the downstream stretch (27) at least one mixing valve (30) comprising at least two infeeds each connected to one of the two parallel ducts (29), and one outfeed connected to the downstream stretch (27), and in that the means for varying the temperature (11) are coupled with one of the two ducts (29), for varying the temperature of the operating fluid in that duct relative to that in the other duct, and in that said two ducts (29) are made either in the initial stretch (22) of each main pipe, or in the shared downstream stretch (27) of the two main pipes.

18. The vitrectomy apparatus according to claim 16, wherein the main pipe (8) comprises at least a downstream stretch (27) which is or can be connected to the supply device (4), (5), and an upstream stretch (28) comprising at least two parallel ducts (29) which are or can be fed with the same operating fluid, there being interposed between the upstream stretch (28) and the downstream stretch (27) at least one mixing valve (30) comprising at least two infeeds each connected to one of the two parallel ducts (29), and one outfeed connected to the downstream stretch (27), and in that the means for varying the temperature (11) are coupled with one of the two ducts (29), for varying the temperature of the operating fluid in that duct relative to that in the other duct, and in that for each main pipe said two ducts (29) are made at least at part of the initial stretch (22) and part of the final stretch (23), in that at said part of the final stretch (23) the two main pipes comprise one of the two ducts (29) which is shared by them, in that the means for varying the temperature (11) are mounted at the shared final stretch (23), and in that the mixing valve (30) comprises three infeeds, connected to each of said ducts (29), and one outfeed connected to the remaining shared final stretch (23), the mixing valve (30) allowing alternatively mixing of the fluid arriving from the shared duct with that arriving from only one of the other two ducts (29).

19. The vitrectomy apparatus according to claim 1, wherein the main pipe (8) comprises at least a downstream stretch (27) which is or can be connected to the supply device (4), (5), and an upstream stretch (28) comprising at least two parallel ducts (29) which are or can be fed with the same operating fluid, there being interposed between the upstream stretch (28) and the downstream stretch (27) at least one mixing valve (30) comprising at least two infeeds each connected to one of the two parallel ducts (29), and one outfeed connected to the downstream stretch (27), and in that the means for varying the temperature (11) are coupled with one of the two ducts (29), for varying the temperature of the operating fluid in that duct relative to that in the other duct.

20. The vitrectomy apparatus according to claim 2, wherein the main pipe (8) comprises at least a downstream stretch (27) which is or can be connected to the supply device (4), (5), and an upstream stretch (28) comprising at least two parallel ducts (29) which are or can be fed with the same operating fluid, there being interposed between the upstream stretch (28) and the downstream stretch (27) at least one mixing valve (30) comprising at least two infeeds each connected to one of the two parallel ducts (29), and one outfeed connected to the downstream stretch (27), and in that the means for varying the temperature (11) are coupled with one of the two ducts (29), for varying the temperature of the operating fluid in that duct relative to that in the other duct, and in that it comprises a temperature detector (14) mounted in the main pipe downstream of the mixing valve (30), the mixing valve (30) being connected to the control unit (21) which is programmed to control the mixing valve (30) depending on what is detected by the temperature detector (14).

21. The vitrectomy apparatus according to claim 2, wherein the means for varying the temperature (11) comprise heating means (12) for increasing the temperature of the operating fluid supplied.

22. The vitrectomy apparatus according to claim 21, wherein the means for varying the temperature (11) also comprise cooling means (13) for reducing the temperature of the operating fluid supplied.

23. The vitrectomy apparatus according to claim 22, wherein the means for varying the temperature (11) comprise at least one secondary pipe (17) mounted on the outside of and coaxially with at least part of the main pipe (8), and which can be fed with a secondary fluid at a controlled temperature for causing a variation in the temperature of the operating fluid, and at least one device (18) for feeding the secondary fluid to the secondary pipe (17), the feeding device (18) being controlled by the control unit (21) and varying the temperature of the secondary fluid.

24. The vitrectomy apparatus according to claim 21, wherein the means for varying the temperature (11) comprise one or more Peltier cells (5) which are associated with said pipe and/or with said supply device (4), (5).

25. The vitrectomy apparatus according to claim 21, wherein the heating means (12) comprise one or more electric heating elements (16) mounted around the main pipe (8).

26. The vitrectomy apparatus according to claim 21, wherein the heating means (12) comprise one or more electric heating elements (16) mounted inside the main pipe (8).

27. The vitrectomy apparatus according to claim 21, wherein the heating means (12) comprise one or more inductors (25) mounted around the main pipe (8) and one or more conductive elements (26) inserted in the main pipe (8) and electromagnetically coupled with the one or more inductors (25) in such a way that the circulation of current in the inductors (25) causes the circulation of eddy currents in the conductive elements (26).

28. The vitrectomy apparatus according to claim 21, wherein the means for varying the temperature (11) comprise at least one secondary pipe (17) mounted on the outside of and coaxially with at least part of the main pipe (8), and which can be fed with a secondary fluid at a controlled temperature for causing a variation in the temperature of the operating fluid, and at least one device (18) for feeding the secondary fluid to the secondary pipe (17), the feeding device (18) being controlled by the control unit (21) and varying the temperature of the secondary fluid.

29. The vitrectomy apparatus according to claim 2, wherein the means for varying the temperature (11) comprise at least one secondary pipe (17) mounted on the outside of and coaxially with at least part of the main pipe (8), and which can be fed with a secondary fluid at a controlled temperature for causing a variation in the temperature of the operating fluid, and at least one device (18) for feeding the secondary fluid to the secondary pipe (17), the feeding device (18) being controlled by the control unit (21) and varying the temperature of the secondary fluid.

30. The vitrectomy apparatus according to claim 2, wherein the means for varying the temperature (11) are at least partly mounted around at least part of said main pipe (8) for varying the temperature of the operating fluid while it flows through the main pipe (8).

31. The vitrectomy apparatus according to claim 2, wherein the feeding means (7) feed at least a first operating fluid and a second operating fluid which are separate, said means respectively comprising a first main pipe (8a) for the first fluid and a second main pipe (8b) for the second fluid, the first main pipe (8a) and the second main pipe (8b) comprising a separate initial stretch (22) and a shared final stretch (23), there being interposed between the initial stretches (23) and the final stretch (23) a three-way (29) switching valve (24) comprising two infeed sections each connected to one of the initial stretches (23), and one outfeed section connected to the final stretch (23).

32. The vitrectomy apparatus according to claim 2, wherein the main pipe (8) comprises at least a downstream stretch (27) which is or can be connected to the supply device (4), (5), and an upstream stretch (28) comprising at least two parallel ducts (29) which are or can be fed with the same operating fluid, there being interposed between the upstream stretch (28) and the downstream stretch (27) at least one mixing valve (30) comprising at least two infeeds each connected to one of the two parallel ducts (29), and one outfeed connected to the downstream stretch (27), and in that the means for varying the temperature (11) are coupled with one of the two ducts (29), for varying the temperature of the operating fluid in that duct relative to that in the other duct.

* * * * *